(12) United States Patent
Kim et al.

(10) Patent No.: US 8,276,632 B2
(45) Date of Patent: Oct. 2, 2012

(54) LABELING AND PREPARATION DEVICE FOR TEST TUBES

(75) Inventors: Sung-Lim Kim, Seoul (KR); Jung-Hun Kang, Seoul (KR); Jin-Sam Ju, Gyeonggi-Do (KR); Kang-Hee Lee, Seoul (KR); Chang-Soon Park, Incheon-Si (KR)

(73) Assignees: Energium Co., Ltd. (KR); Ginus Co., Ltd. (KR)

( * ) Notice: Subject to any disclaimer, the term of this patent is extended or adjusted under 35 U.S.C. 154(b) by 170 days.

(21) Appl. No.: 12/676,713

(22) PCT Filed: Aug. 29, 2008

(86) PCT No.: PCT/KR2008/005075
§ 371 (c)(1),
(2), (4) Date: Mar. 5, 2010

(87) PCT Pub. No.: WO2009/035225
PCT Pub. Date: Mar. 19, 2009

(65) Prior Publication Data
US 2010/0252203 A1 Oct. 7, 2010

(30) Foreign Application Priority Data
Sep. 10, 2007 (KR) .................. 10-2007-0091623

(51) Int. Cl.
*B32B 41/00* (2006.01)
(52) U.S. Cl. ......... 156/361; 156/362; 156/367; 156/368

(58) Field of Classification Search ............ 156/360, 156/361, 362, 367, 368; 422/549, 550, 562, 422/915
See application file for complete search history.

(56) References Cited

U.S. PATENT DOCUMENTS

| | | | |
|---|---|---|---|
| 5,688,361 A | | 11/1997 | Itoh |
| 6,293,750 B1 * | | 9/2001 | Cohen et al. ............... 414/744.4 |
| 2003/0215362 A1 * | | 11/2003 | Sato et al. .................... 422/63 |
| 2004/0231145 A1 * | | 11/2004 | Saito ........................... 29/721 |

FOREIGN PATENT DOCUMENTS

| | | | |
|---|---|---|---|
| JP | 10-59339 A | | 3/1998 |
| JP | 10059339 A | * | 3/1998 |
| JP | 10-139023 A | | 5/1998 |
| JP | 10139023 A | * | 5/1998 |
| JP | 2000-153818 A | | 6/2000 |
| JP | 2000153818 A | * | 6/2000 |
| WO | WO 2006097813 A1 | * | 9/2006 |

* cited by examiner

*Primary Examiner* — George Koch
(74) *Attorney, Agent, or Firm* — Cantor Colburn LLP (57) ABSTRACT

A labeling and preparation device for test tubes. At least one storage section places at least one pallet having a set of test tubes at a preset position. At least one transfer section is disposed above the storage section, and clamps or releases one of the test tubes. A labeling section is disposed below the transfer section, receives the test tubes transferred from the transfer section, and attaches a label having information related to a sample on a circumference of each test tube. An ejection section is disposed below the labeling section, and ejects the test tubes to an outside. A controller controls drivers of the transfer section, the labeling section and the ejection section.

10 Claims, 7 Drawing Sheets

LABELING AND PREPARATION DEVICE FOR TEST TUBES

CROSS-REFERENCED TO RELATED APPLICATION

This application is a National Stage entry of International Application No. PCT/KR2008/005075, filed Aug. 29, 2008, which claims priority to Korean Patent Application No. 10-2007-0091623, filed Sep. 10, 2007, the disclosure of the prior applications is incorporated in its entirety by reference.

TECHNICAL FIELD

The present invention relates, in general, to a device for labeling and preparing test tubes before the test tubes are used at institutes, hospitals, laboratories, etc., and more particularly, to a labeling and preparation device for test tubes, which sequentially transfers the test tubes from among sets of test tubes for collecting blood according to a preset value, attaches labels, on which related information about a sample contained in each test tube is recorded, to the respective test tubes, and thereby sequentially prepares the test tubes.

BACKGROUND ART

As for test tubes used for containing blood, samples of animals, plants, and chemicals for the purpose of clinical examination, biochemical investigation, etc., information about testees or test targets is manually and directly recorded onto the respective test tubes one by one before actual samples from the testees or the test targets are put into the test tubes, thereby preventing the test tubes from being accidentally switched due to the careless mistake of a worker after the actual samples from the testees or the test targets have been put into the test tubes.

Meanwhile, the type of the test tube used for collecting blood from the testee is dependent on the amount, test type, etc. of the collected blood. In cases where a large variety and quantity of blood collection test tubes are treated at general hospitals, institutes, laboratories, etc., mobility for cryogenic storage of the blood collection test tubes is improved by using a pallet on which the same type of test tube in quantities of about 100 to 200 can be loaded.

It takes workers considerable time and effort to record information on the various, numerous test tubes. During the repetition of such work it frequently occurs that information is wrongly recorded.

Moreover, recent use has been made of a device for automatically preparing test tubes, which selects a desired one from a bench of test tubes before the corresponding sample such as blood is put into the test tube, and then attaches a label, which is printed with information about a testee or a test target such as characters or a bar code, to an outer surface of the selected test tube. When using this conventional device, above all, the worker must sort the numerous test tubes one by one, and then load them onto the device. Further, a transfer device and a labeling device must secure flexibility so as to be able to cope with various test tubes. To this end, the transfer device is equipped with a gripper, which results in complication of mechanical configuration, increase in volume, and requires considerable manufacturing costs and installing expenses. Ultimately, the conventional device has no alternative but to be used in the limited environment where a great quantity of test tubes are treated for example at large scale hospitals, institutes, and so on.

DISCLOSURE OF INVENTION

Technical Problem

Accordingly, the present invention has been made in an effort to solve the problems occurring in the related art, and embodiments of the present invention provide a labeling and preparation device for test tubes, which sequentially clamps and transfers the test tubes which are typically used in hospitals, institutes, laboratories, etc., or clamps and transfers the test tubes from pallets on which the test tubes are loaded, and attaches labels, which are transferred in a top-down fashion, to the respective test tubes.

Technical Solution

According to embodiments of the present invention, there is provided a labeling and preparation device for test tubes, which comprises:

at least one storage section placing at least one pallet, on which a set of test tubes is loaded upright according to a type of the test tube, at a preset position;

at least one transfer section disposed above the storage section, for clamping or releasing one of the test tubes in cooperation with movement on an x-y plane parallel to the pallets and z-axial movement perpendicular to the pallets;

a labeling section disposed below the transfer section, for receiving the test tubes transferred from the transfer section, and attaching a label, on which information related to a sample was previously recorded, on a circumference of each test tube;

an ejection section disposed below the labeling section, for ejecting the test tubes, to which the labels are attached and which are transferred from the labeling section in a top-down fashion, to an outside; and a controller presetting one of the type-specific test tubes placed on the storage section and controlling drivers of the transfer section, the labeling section and the ejection section.

In an embodiment of the present invention, the labeling and preparation device may further comprise a drop transfer passage for guiding the test tubes between the transfer section and the labeling section.

In another embodiment of the present invention, the transfer section may include: an x-axial driver, which includes a pair of x-axial frames having an x-axial length corresponding to that of the storage section disposed below and spaced in parallel apart from each other, driving and driven shafts coupled to opposite ends of the x-axial frames via x-axial belts so as to cooperate with the x-axial belts, and a first driving motor coupled to the driving shaft at an output end thereof; a y-axial driver, which includes a y-axial frame fixed to the x-axial belts so as to cooperate with the x-axial belts in an x-axial direction and having a y-axial width corresponding to that of the storage section disposed below, driving and driven pulleys coupled to opposite ends of the y-axial frame via a y-axial belt so as to cooperate with the y-axial belt, and a second driving motor coupled to the driving pulley at an output end thereof; and a z-axial gripper, which includes a frame fixed to the y-axial belt and moving on the x-y plane, a gripper body installed on the frame and moving up and down with respect to the storage section disposed below it, a third driving motor moving the gripper body in the frame in upward and downward directions, and a clamping means clamping or releasing the test tube in cooperation with the upward or downward movement of the gripper body.

In another embodiment of the present invention, the gripper body may include a movable block coupled to the output end of the third driving motor and moving up and down, a stationary finger fixed on one side of the movable block, and a movable finger facing the stationary finger, coupled on the other side of the movable block, and moving toward or away from the stationary finger to clamp or release the test tube in cooperation with the clamping means.

In another embodiment of the present invention, the clamping means may include: a slant guide, which is fixed to a stationary base on a side of the frame and protrudes upwards to the movable block disposed above to form an inclined face; a rotary segment, which is hinged with a lower surface of the movable block through a hinge axle in a center thereof, is fixed to the movable finger on one side thereof, and has a slide end, supported on the inclined face of the slant guide when the downward movement of the movable block is nearly completed, at an end thereof on the other side thereof; and a pressure spring, which elastically supports one side of a circumference of the rotary segment from the movable block, and causes the movable finger to continue to be pressed toward the stationary finger.

In another embodiment of the present invention, the labeling section may include: a frame; a stop space having an inlet, which receives the transferred test tube released from the transfer section, in a central upper portion of the frame and an outlet directed toward the ejection section disposed below it, and a feed slot into which the labels are fed from a label feeding and recording means disposed on an outside of the labeling section; a rotating roller located on one side of the stop space and rotated by driving of the test tube rotating motor opposite and near the circumference of the test tube received in the stop space; at least one contact roller pressing the test tube received in the stop space and the label inserted between the test tube and the rotating roller on the other side of the stop space and bringing the label and the test tube into close contact with the rotating roller opposite the contact roller; and an opening/closing cam disposed below the outlet of the stop space, supporting a lower end of the test tube to stop the test tube or opens the outlet of the stop space to transfer the test tube to the ejection section disposed below.

In another embodiment of the present invention, the contact roller may be installed in front of a label contacting motor fixed to the frame so as to move a rod toward or away from the stop space perpendicular to the rotating roller opposite the contact roller, preferably in front of a movable bracket supported on an end of the rod of the label contacting motor via an elastic member.

In another embodiment of the present invention, the contact rollers may number two, and the two contact rollers are installed on the movable bracket and are supported on the circumference of the test tube received in the stop space along with the rotating roller at three points.

In another embodiment of the present invention, the opening/closing cam may include: a rotating shaft, which is coupled with a cam rotating motor and is vertically disposed around the outlet of the stop space; and an open recess, which is cut off from the opening/closing cam in a shape of a circular sector having two radial ends. Further, the opening/closing cam may rotate around the rotating shaft and have a radius corresponding to a diameter of the outlet of the stop space.

In another embodiment of the present invention, the opening/closing cam may further include a labeling height adjusting means capable of adjusting a position where the label is attached to the circumference of the test tube received in the stop space.

In another embodiment of the present invention, the labeling height adjusting means may include: a rotating shaft, which is coupled with a cam rotating motor and is vertically disposed around the outlet of the stop space; and an open recess, which is cut off from the opening/closing cam in a shape of a circular sector having two radial ends. Further, the labeling height adjusting means may rotate around the rotating shaft, have a radius corresponding to a diameter of the outlet of the stop space, have a height difference between the cut radial ends, and include an inclined plane extending from one of the radial ends to the other radial end.

According to embodiments of the present invention, the labeling and preparation device directly loads numerous, various commercialized test tubes and pallets on which these test tubes are loaded, so that it can simplify the preparation process of sorting the test tubes one by one, and then loading the sorted test tubes onto the device.

Further, the labeling and preparation device can selectively dispose a storage section and a transfer section in a horizontal or vertical direction in consideration of an installed place, so that it can provide flexibility to an installation environment.

Also, the labeling and preparation device transfers one selected from a set of test tubes in a storage section in a top-down fashion, so that it can simplify the entire construction, thus making it convenient to manage manufacturing costs and maintenance.

In addition, the labeling and preparation device provides for a diversity of transferring and labeling processes of various test tubes, so that it can offer a qualitative advantage.

DESCRIPTION OF SYMBOLS OF THE MAIN PARTS IN THE DRAWINGS 1, 1": storage section
2, 2": transfer section 3: label feeding and recording means
4: labeling section
5: ejection section
6: drop transfer passage
11: pallet
20: x-axial driver
30: y-axial driver
40: z-axial gripper
45: gripper body
50: clamping means
63: rotating roller
64: contact roller
65: opening/closing cam
70: labeling height adjusting means
S: test tube set
s: test tube

MODE FOR THE INVENTION

It should be noted that targets that are to be contained in test tubes used in a preparation device according to an embodiment of the present invention can be applied to a variety of targets such as blood collected from testees (e.g. patients) for use in hospitals, samples of various animals, plants and chemicals for use in institutes or chemical laboratories, and so on. However, in the detailed description of the embodiments of the present invention in conjunction with the accompanying drawings, reference will be made to a process of preparing test tubes, in which various types of blood collected from testees (e.g. patients) are contained and used as samples, as a most exemplary embodiment.

Figure 1:
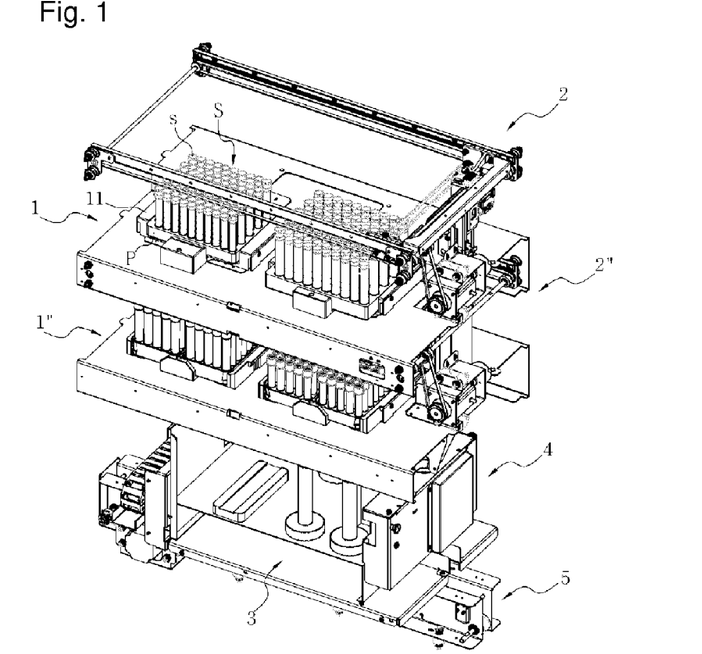
FIG. 1 is a perspective view illustrating construction of a labeling and preparation device for test tubes according to an exemplary embodiment of the present invention.
Figure 2:
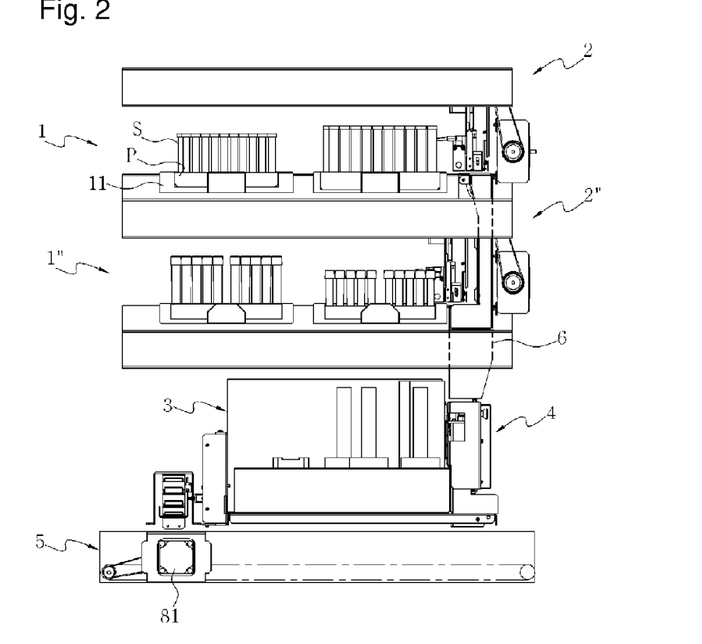
FIG. 2 is a side view illustrating a labeling and preparation device for test tubes.

FIG. 1 is a perspective view illustrating construction of a labeling and preparation device for test tubes for collecting various types of blood according to an exemplary embodiment of the present invention. FIG. 2 is a side view illustrating a labeling and preparation device for test tubes for collecting various types of blood. Referring to FIGS. 1 and 2, the labeling and preparation device for test tubes for collecting various types of blood according to an exemplary embodiment of the present invention is constructed so that storage sections 1 and 1", transfer sections 2 and 2", a labeling section 4, and an ejection section 5 are generally installed in a box-shaped housing, which is not shown.

In addition to these sections, the labeling and preparation device for test tubes includes a controller (not shown), which is preset so as to select the test tube required for a corresponding testee from among the various types of test tubes based on various variables such as desired test object and method of the collected blood, a child, or an adult, and controls driving of the sections.

The storage sections 1 and 1" are disposed on an x-y plane on an upper side of the preparation device, and is provided with at least one seat table 11 on which a pallet P, on which a set of test tubes s is loaded, is placed and fixed in place. The pallet P is provided with a plurality of loading recesses, into which the same types of test tubes s are inserted.

As illustrated, in an embodiment of the present invention, the test tube sets S divided into four types are loaded on the respective pallets P, and then the pallets P are positioned on the seat table 11 in place.

In other words, the seat table 11 installed on each of the storage sections 1 and 1" is manufactured so as to correspond to the pallet P according to a type of test tube s used frequently, and must be designed to cause a change in the position of the pallet P that is positioned in place when the test tubes are clamped using the transfer sections 2 and 2", which will be described below.

Information about the position of the seat table 11 that positions each type of pallet P in place, a size (diameter) and a height (length) of the test tube s that is placed on the seat table 11, the total number of the loaded pallets P, etc. are preset by the controller (not shown).

Further, as illustrated, the seat tables 11 of the storage sections 1 and 1" are constructed so that the pallet P, on which the test tube set S numbering 100 to 120 is generally loaded, is installed on the x-y plane. These seat tables 11 can be disposed in two or more rows in a vertical direction. Of course, the transfer sections 2 and 2", which will be described below, are also disposed so as to correspond to the storage sections 1 and 1" disposed in the vertical direction as described above. In the following description of these transfer sections 2 and 2", in order to help clearly understand the construction thereof, one of the transfer sections 2 and 2" which corresponds to one of the storage sections 1 and 1" will be described.

Figure 3:
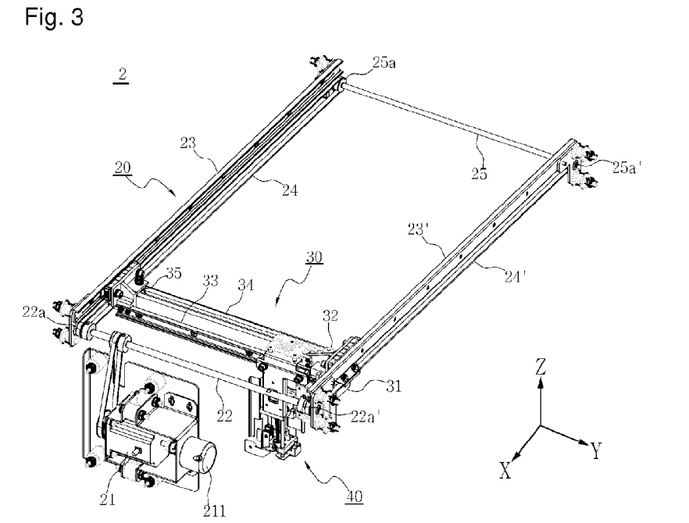
FIG. 3 is a perspective view illustrating the construction of a transfer section.

FIG. 3 is a perspective view illustrating the construction of a transfer section. Referring to FIG. 3, the transfer section 2 is disposed on an upper portion of the storage section 1, and has a driving region on the x-y plane and a z-axial driving region oriented to the storage section 1 disposed below on the basis of an output end thereof (gripper). The transfer section 2 generally includes an x-axial driver 20 driven back and forth in an x-axial direction parallel to the storage section 1 disposed below, a y-axial driver 30 coupled to an output of the x-axial driver 20 and driven left and right in a y-axial direction of the storage section 1, and a z-axial gripper 40 coupled to an output of the y-axial driver 30 and driven up and down in a z-axial direction with respect to the storage section 1.

More specifically, the x-axial driver 20 includes a pair of x-axial frames 23 and 23' having an x-axial length corresponding to that of the storage section 1 disposed below and spaced in parallel apart from each other, driving and driven shafts 22 and 25 coupled to opposite ends of the x-axial frames 23 and 23' via x-axial belts 24 and 24' so as to cooperate with the x-axial belts 24 and 24', and a first driving motor 21 coupled to the driving shaft 22 at an output end thereof and operated backwards and forwards according to an operation signal received from the controller. Among the reference numbers which have not yet been described, 211 indicates an encoder for the first or x-axial driving motor 21 connected to the controller, 22a and 22a' are driving pulleys of the driving shaft 22 around which the x-axial belts 24 and 24' as power transmission members are wound, and 25a and 25a' are driven pulleys of the driven shaft 25 around which the x-axial belts 24 and 24' as power transmission members are wound.

Next, the y-axial driver 30 includes a y-axial frame 33 fixed to the x-axial belts 24 and 24' so as to cooperate with the x-axial belts in an x-axial direction and having a y-axial width corresponding to that of the storage section 1 disposed below, driving and driven pulleys 32 and 35 coupled to opposite ends of the y-axial frame 33 via a y-axial belt 34 so as to cooperate with the y-axial belt 34, and a second driving motor 31 operating the driving pulley 32 in backward and forward directions according to an operation signal received from the controller.

The z-axial gripper 40 includes a frame 42, an upper end of which is fixed to the y-axial belt 34 so as to move on the x-y plane by means of the x-axial and y-axial drivers 20 and 30.

Figure 4:
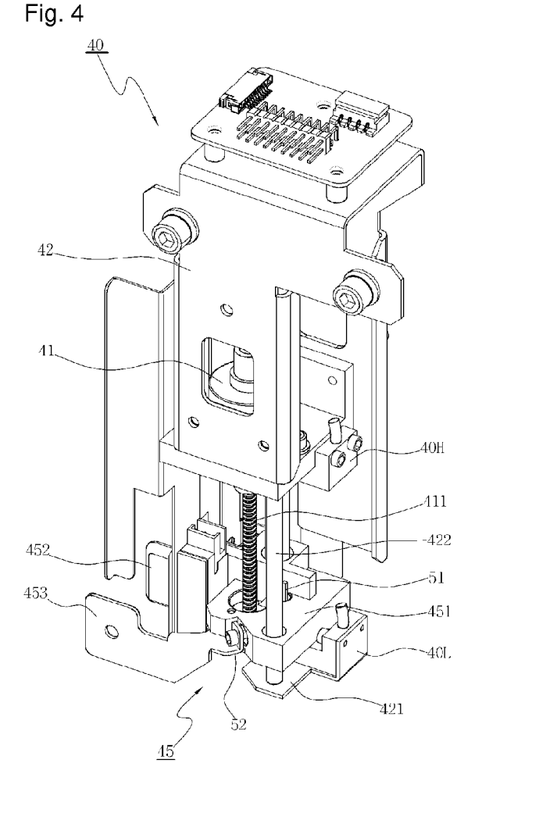
FIG. 4 is a perspective view illustrating the detailed construction of a z-axial gripper.

FIG. 4 is a perspective view illustrating the detailed construction of a z-axial gripper. Referring to FIGS. 3 and 4, the z-axial gripper 40 includes a frame 42 fixed to the y-axial belt 34 of the y-axial driver 30 and moving on the x-y plane by means of the x-axial and y-axial drivers 20 and 30, a gripper body 45 installed on the frame 42 and moving up and down with respect to the storage section 1 disposed below, and a third driving motor 41 moving the gripper body 45 in the frame 42 in upward and downward directions.

This z-axial gripper 40 realizes upward and downward movements of any test tube s, which is to be clamped from the test tube set S placed on the storage section 1, on the x-y plane with respect to the corresponding test tube s and as well it drives for purposes of clamping the test tube s the gripper that is the output end of the transfer section, by moving on the x-y plane as described above.

Figure 5:
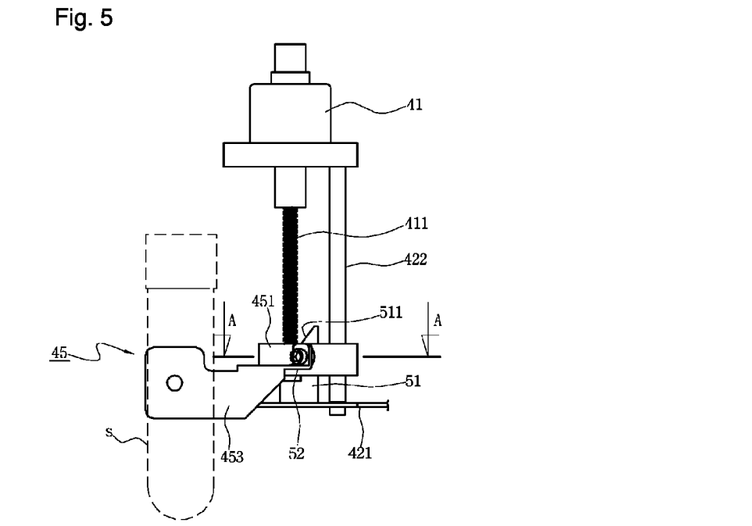
FIGS. 5 and 6 are schematic side views illustrating a point of time when a test tube is clamped by a z-axial gripper and the operation in which the clamped test tube is raised.
Figure 6:
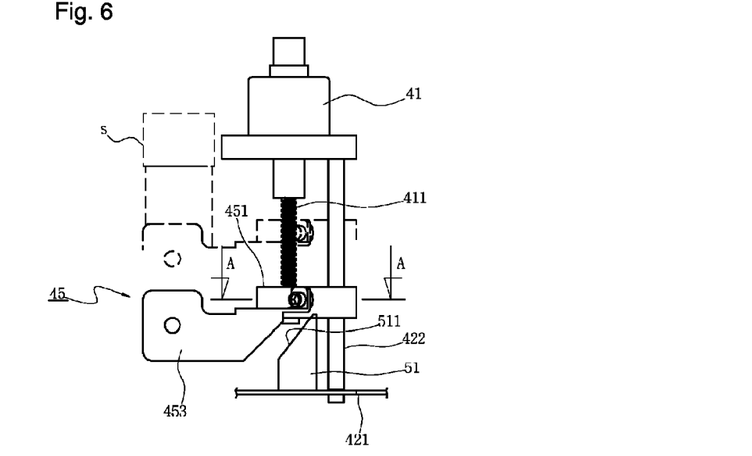
Figure 7:
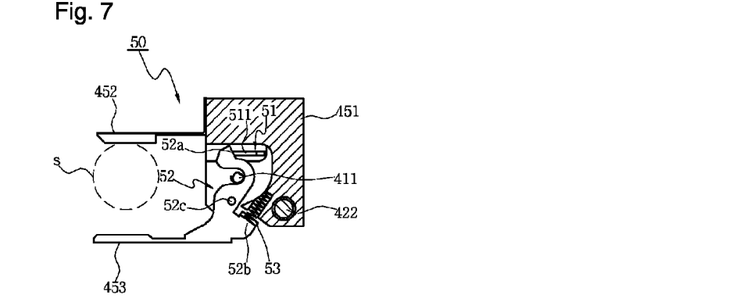
FIG. 7 is a schematic cross-sectional view taken along line A-A of FIG. 5.
Figure 8:
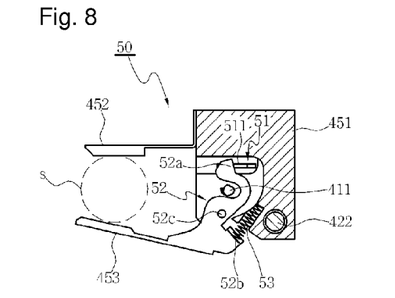
FIG. 8 is a schematic cross-sectional view taken along line A-A of FIG. 6.

FIG. 5 is a schematic side view illustrating a point of time when a test tube is clamped by a z-axial gripper, and FIG. 6 is a schematic side view illustrating the operation in which a test tube is being raised after being clamped by a z-axial gripper. FIG. 7 is a schematic cross-sectional view taken along line A-A of FIG. 5, and FIG. 8 is a schematic cross-sectional view taken along line A-A of FIG. 6.

Referring to FIGS. 4 through 8, the frame 42 has an installation space and an elevation space such that a screw 411 as an output end thereof is raised or lowered therein according to operation of the third driving motor 41 fixed in the upper center thereof, and such that the gripper body 45 installed on one end of the screw 411 moves upwards and downwards in cooperation with the screw 411.

As for the range within which the gripper body 45 moves upwards and downwards along the screw 411 in a vertical or z-axial direction, a height at which the test tube s, a lower end of which is fitted into the pallet P on the storage section 1, can avoid interfering with the movement on the x-y plane of the transfer section 2 after being separated from the pallet P will suffice. Preferably, upper and lower limit sensors 40H and 40L sensing the z-axial driving region are installed at uppermost and lowermost end points up to which the gripper body 45 can move upwards and downwards, and a test tube detection sensor is installed so as to check whether or not the test tube s to be clamped is loaded on the pallet P on the storage section 1. Values detected by these sensors make it possible to promote driving performance of the transfer section 2 by the aid of the controller such that the drivers 20, 30 and 40 can more efficiently move to clamp the test tube.

Continuously, the gripper body 45 moves up and down when the third driving motor 41 is driven, and includes a movable block 451 coupled to the lower end of the screw 411, and a stationary finger 452 fixed on one side of the movable block 451, and a movable finger 453 coupled with a clamping means 50 near the stationary finger 452, and clamping or releasing the test tube s by moving toward or away from the stationary finger 452 in cooperation with the clamping means 50.

Preferably, in order to stably raise or lower the movable block 451, at least one guide rod 422 is additionally installed on the frame 42.

Further, the clamping means 50 includes a slant guide 51, which is installed on a stationary base 421 integrally fixed to a lower end of the frame 42 and protrudes upwards to partly form an inclined face 511, a rotary segment 52, which is hinged with the movable block 451 through a hinge axle 52c in the center thereof, and a pressure spring 53, which is inserted on one side of the movable block 451 and elastically presses a pressure part 52b formed on one side of the circumference of the rotary segment 52. Here, centering on the hinge axle 52c, the movable finger 453 is fixed on one side of the rotary segment 52, while the rotary segment 52 is provided with a slide end 52a, which is supported on the inclined face 511 of the slant guide 51, at an end thereof on the other side thereof.

The clamping means 50 having this construction realizes a clamping force that causes the movable finger 453 to be pivoted around the hinge axle 52c by the pressure spring 53 installed on the movable block 451. When the clamping force caused by the pressure spring 53 is released, the slide end 52a of the rotary segment 52 cooperating with the downward movement of the movable block 451 is pressed in an opposite direction by the inclined face 511 of the slant guide 51 fixedly disposed below the frame 42. Thereby, the movable finger 453 moves away from the stationary finger 452 so as to separate the test tube s clamped between the movable finger 453 and the stationary finger 452 or to maintain an open state for clamping the test tube s.

The operation of the transfer section 2 that realizes the movement on the x-y plane without moving toward or away from the test tube s, the z-axial movement toward the test tube s, and the clamping of the test tube s will be described below with reference to FIGS. 3, and 5 through 8.

First, the pallet P on which the test tube set S is loaded according to a type of test tube is placed on the seat table 11 of the storage section 1, and then the transfer section 2 is driven by an operation signal of the controller, and thus clamps and transfer the test tubes s according to a type and a sequence preset by the controller.

The z-axial gripper 40 is initially kept at a preset position (reference position) on the x-y plane. At this time, the gripper body 45 of the z-axial gripper 40 is lowered and supported on the slant guide 51, thereby entering an open state in which the pressure spring 53 is compressed.

Afterwards, the first driving motor 21 is driven by an operation signal of the controller, and thus moves the y-axial frame 33 toward the test tube s to be clamped in an x-axial direction along the x-axial belts 24 and 24' installed on the x-axial frames 23 and 23'. Then, the second driving motor 31 is driven to move the z-axial gripper 40 in a y-axial direction along the y-axial belt 34 installed on the y-axial frame 33 such that the test tube s to be clamped is positioned between the stationary finger 452 and the movable finger 453 of the z-axial gripper 40 (see FIGS. 5 and 7).

Next, the third driving motor 41 of the z-axial gripper 40 is driven to rotate the screw 411 serving as an output shaft thereof so as to move upwards, thereby raising the gripper body 45 located at a lower end of the screw.

As soon as the gripper body 45 is raised, the rotary segment 52, to which the movable finger 453 installed on the movable block 451 is fixed, is guided upwards along the inclined face 511 of the slant guide 51 through the slide end 52a of the end thereof. Thereby, the movable finger 453 is pivoted around the hinge axle 52c so as to correspond to an expansion level of the pressure spring 53 pressing the pressure part 52b formed on one side of the circumference of the rotary segment 52, thereby moving toward the stationary finger 452. Thus, the test tube s is clamped between the stationary finger 452 and the movable finger 453 (see FIGS. 6 and 8).

After the clamping of the test tube s of the gripper body 45 is completed, the third driving motor 41 continues to raise the gripper body 45, thereby separating the clamped test tube s from the pallet P in an upward direction.

Afterwards, after the upward movement of the z-axial gripper 40 is completed, the second driving motor 31 and the first driving motor 21 are reversely driven again, so that the z-axial gripper 40 is returned to the preset position (reference position) on the x-y plane.

After the z-axial gripper 40 is returned to the preset position (reference position) with the test tube s clamped, the third driving motor 41 is driven to move the gripper body 45 in a downward direction. During the downward movement, the slide end 52a of the rotary segment 52 installed on the movable block 451 comes into close contact with the inclined face 511 of the slant guide 51 disposed below, and thus compresses the pressure spring 53, so that the rotary segment 52 is reversely rotated around the hinge axle 52c. The movable finger 453 cooperating with the rotary segment moves away from the stationary finger 452, so that the test tube s clamped between the fingers is separated and dropped.

In this manner, this transfer section 2 sequentially repeats a series of transfer processes with respect to the test tubes s preset for the controller.

Meanwhile, referring to FIGS. 1 and 2 again, the test tube s, which is clamped and displaced to the reference position by the transfer section 2 and then is separated and dropped from the gripper body 45, is transferred to the labeling section 4 installed below the transfer section 2. To this end, there is a drop transfer passage 6 for the test tubes s disposed between the gripper body 45 of the transfer section 2 and the labeling section 4 installed below the transfer section 2.

Figure 9:
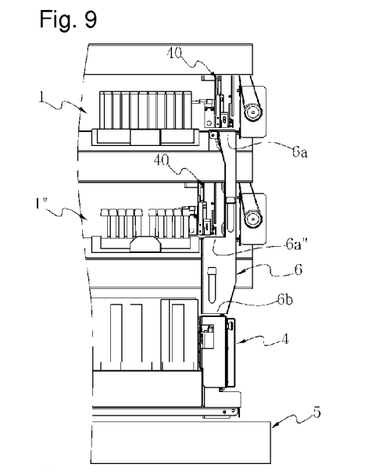
FIG. 9 is a partial side view illustrating a drop transfer passage in a labeling and preparation device for test tubes according to an exemplary embodiment of the present invention.

According to an embodiment of the present invention, as illustrated in FIG. 9, this drop transfer passage 6 has two inlets 6a and 6a" corresponding to the number of the storage sections 1 and 1" and the transfer sections 2 and 2" which are installed at two places in a vertical direction, and a single outlet 6b for sequentially guiding the test tubes s toward the labeling section 4.

Preferably, the drop transfer passage 6 is provided, on an inner surface thereof, with a flexible material having elasticity such as fabric, plastic, etc. in order to prevent damage of the test tube falling toward the outlet 6b due to weight of the test tube.

Figure 11:
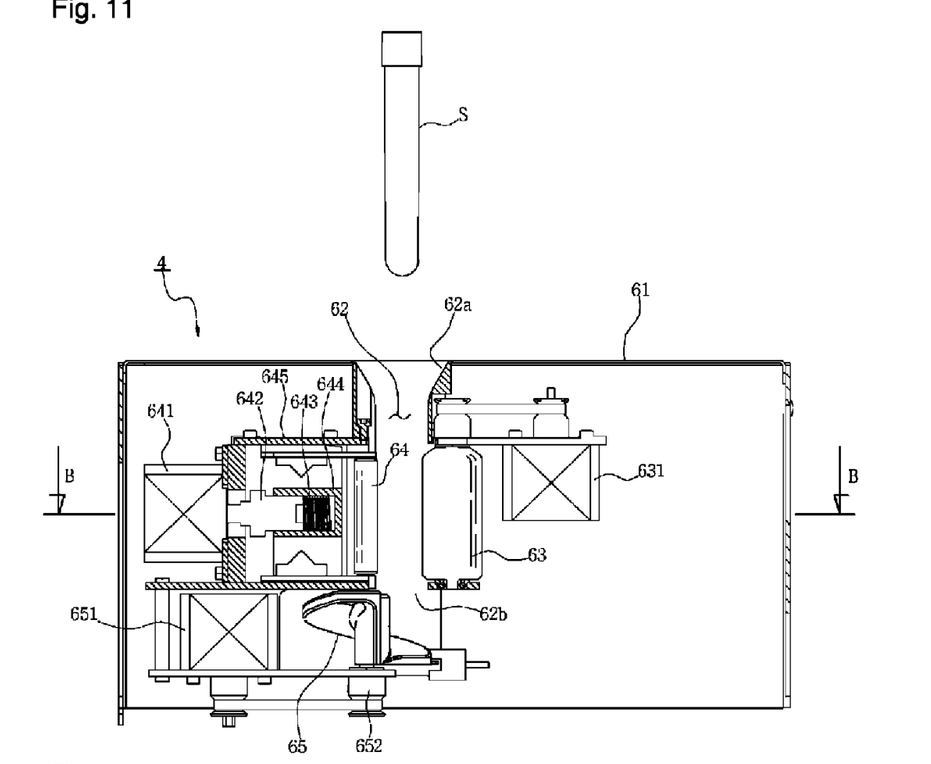
FIG. 11 is a side view illustrating the construction of a labeling section according to an embodiment of the present invention.
Figure 12:
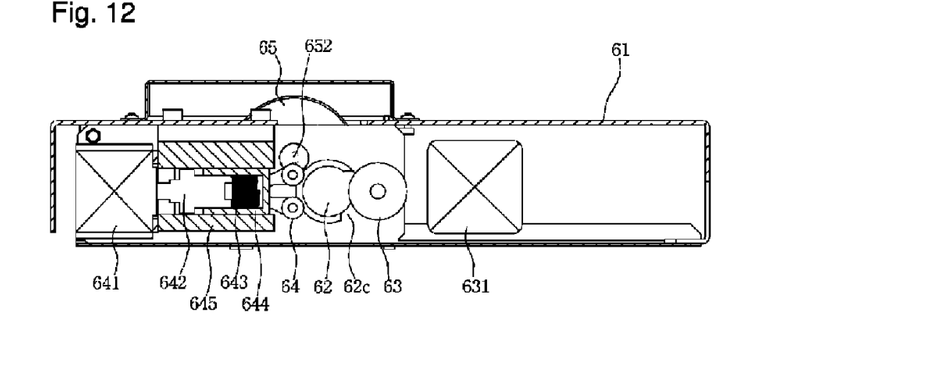
FIG. 12 is a cross-sectional view taken along line B-B of FIG. 11.
Figure 13:
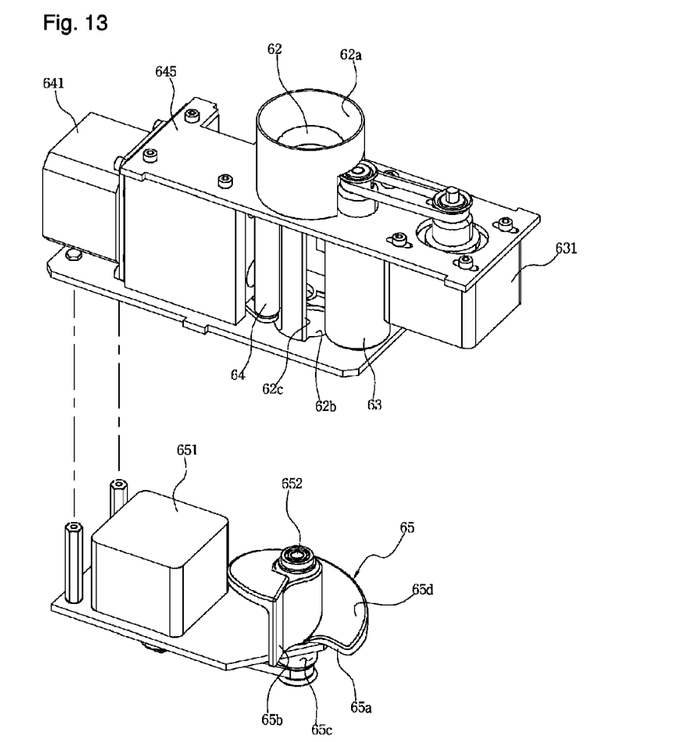
FIG. 13 is a disassembled perspective view illustrating a labeling section according to an embodiment of the present invention.
Figure 14:
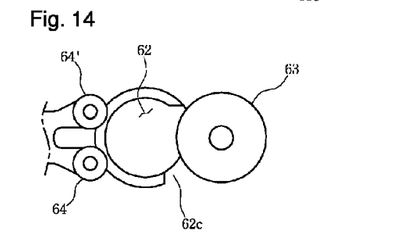
FIGS. 14 through 16 are schematic top plan views illustrating the operation of a labeling section according to an embodiment of the present invention.
Figure 15:
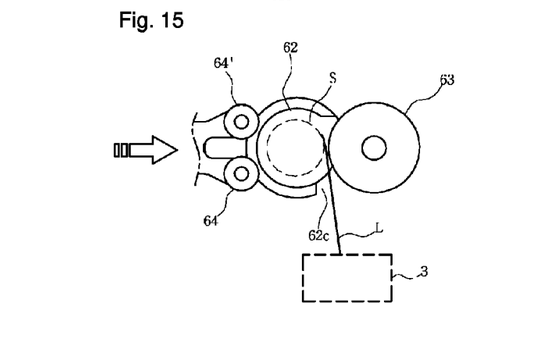
Figure 16:
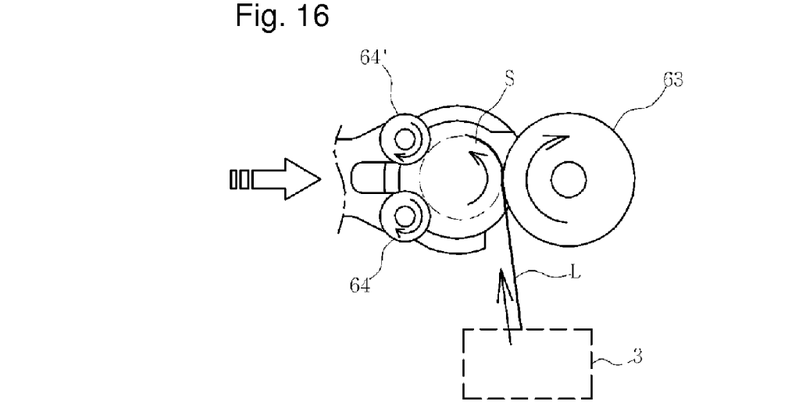

FIG. 11 is a side view illustrating the construction of a labeling section according to an embodiment of the present invention. FIG. 12 is a cross-sectional view taken along line B-B of FIG. 11. FIG. 13 is a disassembled perspective view illustrating a labeling section according to an embodiment of the present invention. FIGS. 14 through 16 are schematic top plan views illustrating the operation of a labeling section according to an embodiment of the present invention. According to an embodiment of the present invention, the labeling section 4 is for attaching a label, on which necessary information related to a testee is recorded from a label recording means for recording the related information on the label, to the corresponding test tube s. The labeling section 4 is disposed between the drop transfer passage 6 through which the test tubes s dropped from the transfer sections 2 and 2" and the ejection section 5.

Figure 10:
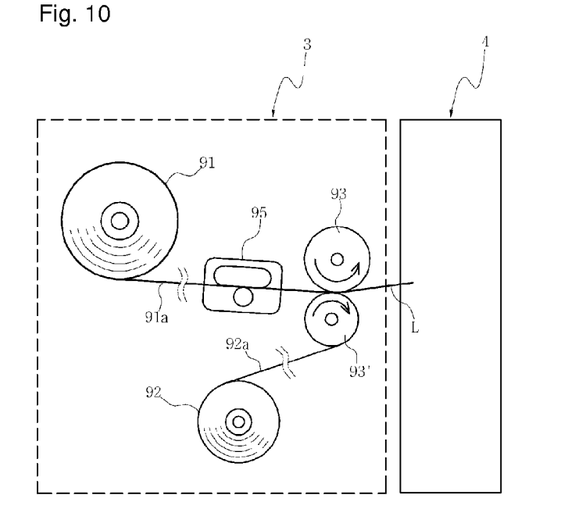
FIG. 10 illustrates a typical label feeding and recording means.

First, prior to a detailed description of the labeling section, referring to FIG. 10, the labeling section 4 is provided with a label feeding and recording means 3 on the outside thereof which continues to feed labels and records information related to a testee preset by the controller on the fed labels. As illustrated in FIGS. 1 and 2, the label feeding and recording means 3 feeds the labels to an inner side of the labeling section 4, and is disposed below the storage section 1. Briefly describing the label feeding and recording means 3, the label feeding and recording means 3 includes a feed paper roll 91 to which labels 91a (prior to recording) are attached, and a release paper roll 92 recovering release paper 92a separated from the label paper roll 91. At this time, the release paper roll 92 is adopted as a driving roll, and cooperates with the label paper roll 91. Further, a recording means 95 is disposed between the label paper roll 91 and the release paper roll 92 in order to previously record the testee related information received from the controller in turn before the labels are fed to the labeling section 4. These labels L on which the testee related information is recorded are fed to the labeling section 4 through feed rollers 93 and 93'. Hereinafter, a more concrete configuration of the label feeding and recording means 3 is well known, and so a detailed description thereof will be omitted.

Now, referring to FIGS. 11 and 14 through 16 again, the labeling section 4 includes a frame 61, a through-hole-like stop space 62 formed between central upper and lower portions of the frame 61 and having an inlet 62a in the central upper portion of the frame which receives the dropped test tube s and faces the outlet 6b of the drop transfer passage 6 disposed above, and an outlet 62b in the central lower portion of the frame, a rotating roller 63 located on one side of the stop space 62 and coming into close contact with the test tube s received in the stop space 62, the rotating roller 63 with the label L inserted from the label feeding and recording means 3 in between, a contact roller 64 pressing a circumference of the test tube s received in the stop space 62 on the opposite side of the rotating roller 63 to thereby bring the label L and the test tube s into close contact with the rotating roller 63. An opening/closing cam 65 for supporting the lower end of the test tube s while the test tube s is being stopped and labeled is disposed below the outlet 62b of the stop space 62.

In detail, the stop space 62 has a cavity greater than a diameter of the test tube s received from the inlet 62a to the interior thereof in a top-down fashion, and thus can receive the test tubes s having various sizes. Preferably, the inlet 62a of the stop space 62 is tapered so as to become wide in an upward direction, thereby guiding drop transfer of the test tube s falling from the drop transfer passage 6. Further, the interior of the stop space 62 partly serves as a feed slot 62c into which the labels L are fed from the label feeding and recording means 3 disposed on the outside of the labeling section.

The rotating roller 63 is rotatably installed on the frame 61, is disposed such that a part of the circumference thereof at least protrudes to the inside of the stop space 62, and is rotated by operation of a test tube rotating motor 631. At this time, the rotating roller 63 that partly protrudes to the inside of the stop space 62 is tapered at an upper edge thereof, thereby preventing the falling test tube s from being damaged by dashing against the upper edge thereof.

The contact roller 64 is opposite to the rotating roller 63. Thus, the contact roller 64 presses the test tube s to which the label L is attached toward the rotating roller 63 during attaching the label L, thereby providing a compression force required to attach the label L. Further, the contact roller 64 guides the test tube s so as to be rotated during attaching the label L in cooperation with the rotating roller 63. As illustrated in FIGS. 14 through 16, preferably, two contact rollers 64 are disposed so as to come into close contact with the circumference of the test tube s, so that they support the circumference of the test tube s rotated along with the rotating roller 63 at three points so as to realize the stable rotation of the test tube s.

These contact rollers 64 are installed in front of a label contacting motor 641 which is fixed to the frame 61 so as to advance a rod 642 toward the stop space 62, particularly in front of a movable bracket 644 supported on an end of the rod 642 of the label contacting motor via an elastic member 643. This movable bracket 644 is guided by a guide bracket 645 fixed to the frame 61 so as to slide back and forth with respect to the stop space 62 along with the contact rollers 64.

The opening/closing cam 65 is disposed on a lower side of the frame 61, and opens/closes the outlet 62b of the stop space 62 of the frame 61. Thus, the opening/closing cam 65 maintains an opened or closed state of the outlet 62b of the stop space 62 on the basis of an amount of rotation caused by operation of a cam rotating motor 651 connected to a rotating shaft 652 thereof. More specifically, the opening/closing cam 65 supports the lower end of the test tube s, which is received in the stop space 62 and to which the label is to be attached, and maintains the outlet 62b of the stop space 62 in the closed state such that the rotating roller 63 and the contact rollers 64 are driven to attach the label to the test tube s, or opens the outlet 62b of the stop space 62 to transfer the test tube s having the attached label to the ejection section 5 disposed below it in a top-down fashion.

Figure 17:
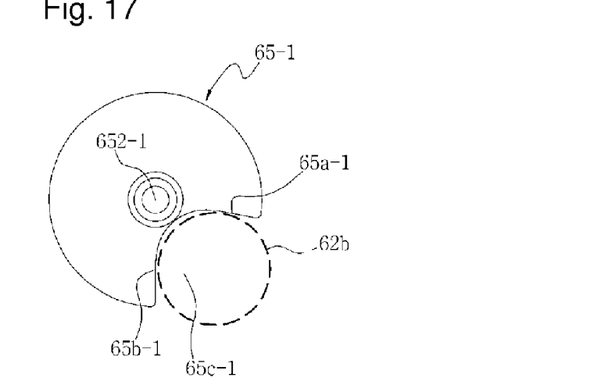
FIGS. 17 and 18 illustrate the construction of an opening/closing cam of a labeling section.

Meanwhile, FIG. 17 is a schematic top plan view illustrating an opening/closing cam according to another embodiment of the present invention. Referring to FIGS. 11 and 17, the opening/closing cam 65-1 according to another embodiment includes a rotating shaft 652-1, which is rotated by the cam rotating motor and is disposed around the outlet 62b of the stop space 62. The opening/closing cam 65-1 rotates around the rotating shaft 652-1, has a radius corresponding to a diameter of the outlet 62b of the stop space 62, and has an open recess 65c-1 that is cut off from the opening/closing cam in the shape of a circular sector having two radial ends 65a-1 and 65b-1.

Of course, in another embodiment, the opening/closing cam 65-1 also opens or closes the outlet 62b of the stop space 62 on the basis of an amount of rotation caused by operation of the cam rotating motor. Thus, the opening/closing cam 65-1 supports the test tube s in a closed state of the outlet 62b of the stop space 62 such that the label is attached to the test tube s, or opens the outlet 62b of the stop space 62 to transfer the test tube s having the attached label to the ejection section 5 disposed below in a top-down fashion.

Figure 18:
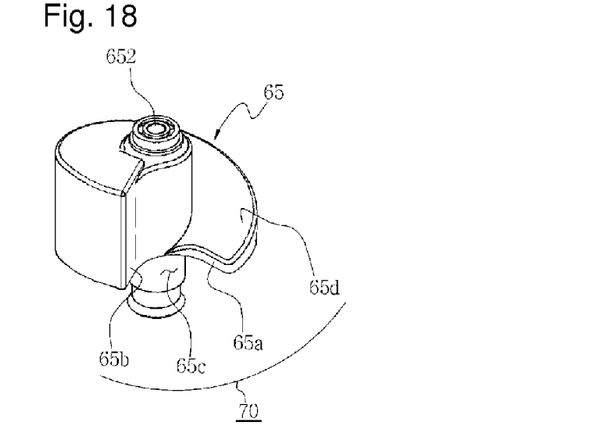

FIG. 18 is a perspective view illustrating an opening/closing cam according to another embodiment of the present invention. Referring to FIGS. 11 and 18, as described above, the opening/closing cam 65 includes a labeling height adjusting means 70 for the test tube s so as to be able to constantly maintain the position where the label L is attached to the circumference of the test tube s at all times, in consideration of the size of the test tube s (generally, the test tubes for collecting blood have different lengths (heights) according to a test type and a testee) transferred from the storage sections 1 and 1" holding various test tube sets S on the basis of a preset value of the controller.

In detail, the labeling height adjusting means 70 includes a rotating shaft 652, which is rotated by the cam rotating motor 651 and is disposed around the outlet 62b of the stop space 62. The opening/closing cam 65 rotates around the rotating shaft 652, has a radius corresponding to a diameter of the outlet 62b of the stop space 62, and has an open recess 65c that is cut off from the opening/closing cam in the shape of a circular sector having two radial ends 65a-1 and 65b-1. The labeling height adjusting means 70 has a height difference between the cut radial ends 65a and 65b, and is provided with an inclined plane 65d extending from one 65a of the radial ends to the other radial end 65b in a spiral shape.

This inclined plane 65 has a different height when supporting the lower end of the test tube s according to an amount of rotation of the cam rotating motor 651. As such, the heights of the test tubes s, each of which is received in the stop space 62 and to which the label is attached, and the heights of the labels attached to the test tubes s having different sizes are controlled equally or differently.

The operation of the labeling section having the aforementioned construction will be described below.

The drivers of the labeling section 4, i.e. the test tube rotating motor 631, the label contacting motor 641 and the cam rotating motor 651, and the driver (not shown) of the label feeding and recording means 3 installed outside the labeling section 4 initially receive the operation signal from the controller. At this time, the recording means 95 functions to previously record related information on the label before the corresponding test tube s is transferred to the labeling section 4 from the storage section 1 and 1" through the transfer sections 2 and 2". In the process of the initial operation of the labeling and preparation device, a leading end of the label paper roll around which the recorded labels are wound is inserted into the feed slot 62c formed in the stop space 62 of the labeling section 4.

Further, before the test tube s enters the stop space 62, the rotating roller 63 connected with the test tube rotating motor 631 maintains a stop state, the label contacting motor 641 maintains the state in which the output end thereof, i.e. the rod 642, is contracted, and the opening/closing cam 65 connected with the cam rotating motor 651 maintains a closed state with respect to the outlet 62b of the stop space 62.

In this initial state, the test tube s dropped from the outlet 6b of the drop transfer passage 6 is received into the stop space 62 through the inlet 62a of the labeling section 4 disposed below, and thus the lower end of the test tube s is supported on the upper surface of the opening/closing cam 65 in a stop state.

At this time, an amount of rotation of the opening/closing cam 65 is controlled through the cam rotating motor 651 according to information about a size (height) of the test tube s corresponding to testee related information received from the controller, and a height of the inclined plane 65d of the opening/closing cam 65 on which the lower end of the test tube s is supported is adjusted. Thereby, the heights of the labels attached to the circumferences of the various test tubes s can be equal to each other. As a result, among the numerous test tubes uniformly loaded on the pallet P, a desired test tube s can be easily found. Further, the beauty of the loaded test tubes is also improved. Of course, a position where the label is attached can be arbitrarily adjusted as needed through this opening/closing cam 65 when the test tube is used.

Continuously, although not shown, a test tube detection sensor for determining whether or not the test tube s exists is added to the stop space 62. Thereby, it is checked through the test tube detection sensor whether or not the test tube s is received. If the test tube s is received, the rod 642 of the label contacting motor 641 is stretched through a signal of the controller, and thus the contact rollers 64 cooperating with the rod of the label contacting motor press the circumference of the test tube s received in the stop space 62, thereby coming into close contact with the label L and the test tube s toward the rotating roller 63 opposite the contact rollers.

Further, the driving conditions of this label contacting motor 641 can be dependent on the size (diameter) of the corresponding test tube s. However, by means of the elastic supporting means of the contact rollers 64 using the elastic member 643 according to an embodiment of the present invention, a compression force required to attach the label L without overloading the test tube s within an elastic range of the elastic member 643 can be sufficiently realized although the same driving conditions are typically required for various test tubes having a predetermined diameter difference.

After the compression of the contact rollers 64 is completed, the rotating roller 63 is rotated by operation of the test tube rotating motor 631, and thereby the test tube s is rotated along with the label L interposed between the rotating roller 63 and the test tube s. Thus, the label L is attached to the circumference of the test tube s.

The contact rollers 64, which support the circumference of the test tube s rotated along with the rotating roller 63 at three points, are rotated in cooperation with the rotating roller, exert lasting compression owing to a supporting force caused by the elastic member 643, and thus provide the compression force required to attach the label.

In this manner, after the test tube s is rotated enough to attach the label L, the rotating roller 63 is stopped again. Afterwards, the contact rollers 64 opposite the rotating roller are returned to their original positions due to contraction of the rod 642 of the label contacting motor 641.

Then, the test tube s, to which the label has been attached, is transferred toward the ejection section 5 disposed below through the open recess 65*c* of the opening/closing cam 65 rotated by the operation of the cam rotating motor 651.

After the test tube s, to which the label has been attached, is transferred, the cam rotating motor 651 recognizes a type of the next test tube s preset by the controller, and thus rotates the opening/closing cam 65 so as to be returned in a closed state.

As described above, the labeling section 4 sequentially repeats a series of labeling processes with respect to a preset list of corresponding test tubes s in cooperation with the transfer sections 2 and 2" according to a value preset for the controller with respect to one test tube s.

The test tube s, which is transferred downwards through the outlet 62*a* of the stop space 62 of the labeling section 4 after the label is attached thereto, moves to the ejection section 5 disposed below the labeling section 4, and then is discharged to the outside of the labeling and preparation device through a conveyer. The test tube s is sent to a place where the use of the test tube s having the label recorded with corresponding related information is required.

In FIG. 2, a reference number 81, which has not yet been described, indicates a driving motor for driving the conveyer of the ejection section 5.

Although an exemplary embodiment of the present invention has been described for illustrative purposes, those skilled in the art will appreciate that various modifications, additions and substitutions are possible, without departing from the scope and spirit of the invention as disclosed in the accompanying claims.

The invention claimed is:

1. A labeling and preparation device for test tubes, comprising:
    at least one storage section positioned on a first layer and placing at least one pallet, on which a set of test tubes is loaded upright according to a type of a test tube, at a preset position;
    at least one transfer section positioned on a second layer and selecting at least one test tube from the set of the test tubes in cooperation with movement on an x-y plane parallel to the pallets and clamping or releasing the at least one selected test tube in cooperation with z-axial movement perpendicular to the pallets;
    a labeling section positioned on a third layer and receiving the at least one selected test tube transferred from the transfer section, and attaching a label, on which information related to a sample was previously recorded, on a circumference of the at least one selected test tube positioned in a through-hole-like stop space of the labeling section, the stop space having a cavity greater than a diameter of the test tube transferred from the transfer section and being tapered in a downward direction so that a width of an upper portion of the stop space is wider than a width of a lower portion thereof, thereby guiding drop transfer of the test tube from the transfer section in the upper portion of the stop space and stopping the test tube in the lower portion thereof;
    an ejection section positioned on a fourth layer and ejecting the at least one selected test tube, to which the label is attached and which is transferred from the labeling section, to an outside;
    a controller presetting one of the type-specific test tubes placed on the storage section and controlling drivers of the transfer section, the labeling section and the ejection section; and
    a drop transfer passage between the transfer section and the labeling section, the at least one selected test tube being dropped downward through the drop transfer passage due to weight of the at least one selected test tube, wherein the drop transfer passage is provided, on an inner surface thereof, with a flexible material having elasticity in order to prevent damage of the test tube when dropped downward, and
    wherein the first through the fourth layers are positioned vertically on top of one another such that the at least one selected test tube is transferred between the transfer section, the labeling section, and the ejection section in a top-down fashion.

2. The labeling and preparation device as set forth in claim 1, wherein the transfer section includes:
    an x-axial driver, which includes a pair of x-axial frames having an x-axial length corresponding to that of the storage section positioned on the first layer and spaced in parallel apart from each other, driving and driven shafts coupled to opposite ends of the x-axial frames via x-axial belts so as to cooperate with the x-axial belts, and a first driving motor coupled to the driving shaft at an output end thereof;
    a y-axial driver, which includes a y-axial frame fixed to the x-axial belts so as to cooperate with the x-axial belts in an x-axial direction and having a y-axial width corresponding to that of the storage section positioned on the first layer, driving and driven pulleys coupled to opposite ends of the y-axial frame via a y-axial belt so as to cooperate with the y-axial belt, and a second driving motor coupled to the driving pulley at an output end thereof; and
    a z-axial gripper, which includes a frame fixed to the y-axial belt and moving on the x-y plane, a gripper body installed on the frame and moving up and down with respect to the storage section positioned on the first layer, a third driving motor moving the gripper body in the frame in upward and downward directions, and a clamping means clamping or releasing the at least one selected test tube in cooperation with the upward or downward movement of the gripper body.

3. The labeling and preparation device as set forth in claim 2, wherein the gripper body includes a movable block coupled to the output end of the third driving motor and moving up and down, a stationary finger fixed on one side of the movable block, and a movable finger facing the stationary finger, coupled on the other side of the movable block, and moving toward or away from the stationary finger to clamp or release the at least one selected test tube in cooperation with the clamping means.

4. The labeling and preparation device as set forth in claim 2 or 3, wherein the clamping means includes:
    a slant guide, which is fixed to a stationary base on a side of the frame and protrudes upwards to the movable block disposed above to form an inclined face;
    a rotary segment, which is hinged with a lower surface of the movable block through a hinge axle in a center thereof, is fixed to the movable finger on one side thereof, and has a slide end, supported on the inclined face of the slant guide when the downward movement of the movable block is nearly completed, at an end thereof on the other side thereof; and a pressure spring, which elastically supports one side of a circumference of the rotary segment from the movable block, and causes the movable finger to continue to be pressed toward the stationary finger.

5. The labeling and preparation device as set forth in claim 1, wherein the labeling section includes:

a frame;

the stop space having an inlet, which receives the transferred at least one selected test tube released from the transfer section through the drop transfer passage, the inlet being positioned in a central upper portion of the frame, and an outlet directed toward the ejection section positioned on the fourth layer, and a feed slot into which the labels are fed from a label feeding and recording means disposed on an outside of the labeling section;

a rotating roller located on one side of the stop space and rotated by driving a test tube rotating motor opposite and near the circumference of the test tube received in the stop space;

at least one contact roller pressing the test tube received in the stop space and the label inserted between the test tube and the rotating roller on the other side of the stop space and bringing the label and the test tube into close contact with the rotating roller opposite the contact roller; and an opening/closing cam disposed below the outlet of the stop space, supporting a lower end of the test tube to stop the test tube or open the outlet of the stop space to transfer the test tube to the ejection section positioned on the fourth layer.

6. The labeling and preparation device as set forth in claim 5, wherein the contact roller is installed in front of a label contacting motor fixed to the frame so as to move a rod toward or away from the stop space perpendicular to the rotating roller opposite the contact roller, and in front of a movable bracket supported on an end of the rod of the label contacting motor via an elastic member.

7. The labeling and preparation device as set forth in claim 5 or 6, wherein the contact roller numbers two, and the two contact rollers are installed on the movable bracket and are supported on the circumference of the test tube received in the stop space along with the rotating roller at three points.

8. The labeling and preparation device as set forth in claim 5, wherein the opening/closing cam includes:

a rotating shaft, which is coupled with a cam rotating motor and is vertically disposed around the outlet of the stop space; and an open recess, which is cut off from the opening/closing cam in a shape of a circular sector having two radial ends, and the opening/closing cam rotates around the rotating shaft and has a radius corresponding to a diameter of the outlet of the stop space.

9. The labeling and preparation device as set forth in claim 5, wherein the opening/closing cam further includes a labeling height adjusting means capable of adjusting a position where the label is attached to the circumference of the test tube received in the stop space.

10. The labeling and preparation device as set forth in claim 9, wherein the labeling height adjusting means includes:

a rotating shaft, which is coupled with a cam rotating motor and is vertically disposed around the outlet of the stop space; and an open recess, which is cut off from the opening/closing cam in a shape of a circular sector having two radial ends, and the labeling height adjusting means rotates around the rotating shaft, has a radius corresponding to a diameter of the outlet of the stop space, has a height difference between the cut radial ends, and includes an inclined plane extending from one of the radial ends to the other radial end.

* * * * *